US012805764B2

(12) United States Patent
Sliozberg et al.

(10) Patent No.: US 12,805,764 B2
(45) Date of Patent: Nov. 24, 2026

(54) METHOD FOR MANUFACTURING A SENSOR BASE PLATE FOR AN IN VIVO ANALYTE SENSING DEVICE

(71) Applicant: Roche Diabetes Care, Inc., Indianapolis, IN (US)

(72) Inventors: Kirill Sliozberg, Mannheim (DE); Alexander Steck, Hirschberg (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 762 days.

(21) Appl. No.: 18/190,816

(22) Filed: Mar. 27, 2023

(65) Prior Publication Data

US 2023/0233111 A1 Jul. 27, 2023

Related U.S. Application Data

(63) Continuation of application No. PCT/EP2021/076431, filed on Sep. 27, 2021.

(30) Foreign Application Priority Data

Sep. 28, 2020 (EP) .................................... 20198696

(51) Int. Cl.
*H01S 4/00* (2006.01)
*A61B 5/145* (2006.01)
*A61B 5/1486* (2006.01)

(52) U.S. Cl.
CPC ........ *A61B 5/14532* (2013.01); *A61B 5/1486* (2013.01); *A61B 2562/12* (2013.01)

(58) Field of Classification Search
CPC .............. A61B 5/14532; A61B 5/1486; A61B 5/14865; A61B 2562/043; A61B 2562/12; A61B 2562/164; A61B 2562/166
See application file for complete search history.

(56) References Cited

U.S. PATENT DOCUMENTS

| | | | |
|---|---|---|---|
| 9,610,034 B2 | 4/2017 | Heller et al. | |
| 10,736,553 B2 * | 8/2020 | Lucisano | A61F 2/442 |
| 11,806,141 B2 * | 11/2023 | Moein | A61B 5/1486 |
| 11,883,164 B2 * | 1/2024 | Kamath | A61B 5/68335 |
| 2012/0109010 A1 | 5/2012 | Sato et al. | |

(Continued)

FOREIGN PATENT DOCUMENTS

| | | |
|---|---|---|
| EP | 3 001 952 A1 | 4/2016 |
| WO | WO 03/044816 A1 | 5/2003 |

OTHER PUBLICATIONS

International Search Report and Written Opinion of the International Searching Authority, PCT/EP2021/076431, Nov. 29, 2021, 9 pages.

(Continued)

*Primary Examiner* — Paul D Kim
(74) *Attorney, Agent, or Firm* — Bose McKinney & Evans LLP

(57) ABSTRACT

A method of manufacturing an in vivo analyte sensing device, which is adapted for detecting at least one analyte in a body fluid or tissue and an in vivo analyte sensing device obtainable by the manufacturing method is disclosed. Also disclosed is a method of manufacturing a sensor base plate and a sensor base plate obtainable by the manufacturing method. The sensor base plate may be used for the manufacture of an in vivo analyte sensing device.

9 Claims, 2 Drawing Sheets

(56) References Cited

U.S. PATENT DOCUMENTS

| | | | | |
|---|---|---|---|---|
| 2014/0371559 | A1 | 12/2014 | Etzkorn et al. | |
| 2018/0353087 | A1 | 12/2018 | Oode et al. | |
| 2019/0117131 | A1 | 4/2019 | Halac et al. | |
| 2020/0245907 | A1 | 8/2020 | List | |
| 2023/0301556 | A1 * | 9/2023 | Stram ................ | G01N 27/4163 |

OTHER PUBLICATIONS

Afsarimanesh et al., Interdigital Sensors: Biomedical, Environmental and Industrial Applications, Sensors and Actuators A: Physical, Feb. 28, 2020, vol. 305, pp. 1-18.

* cited by examiner

METHOD FOR MANUFACTURING A SENSOR BASE PLATE FOR AN IN VIVO ANALYTE SENSING DEVICE

RELATED APPLICATIONS

This application is a continuation of International Patent Application No. PCT/EP2021/076431, filed Sep. 27, 2021, which claims priority to EP 20 198 696.5, filed Sep. 28, 2020, both of which are hereby incorporated herein by reference.

BACKGROUND

This disclosure relates to a method of manufacturing a sensor base plate and a sensor base plate obtainable by the manufacturing method. The sensor base plate may be used for the manufacture of an in vivo analyte sensing device.

Monitoring the concentrations of physiologically relevant analytes in body fluids or body tissues plays an important role in the prevention, control and treatment of various diseases such as diabetes mellitus.

Diabetes mellitus is a disorder in which the beta cells of the pancreas cannot produce sufficient amounts of insulin (type I) or in which insulin is not effective (type II). Without appropriate medication, the blood glucose level cannot be regulated adequately, which in turn may lead to serious pathological conditions.

In order to avoid the occurrence of these pathological conditions and the damages associated therewith, the blood glucose level of diabetic subjects needs to be monitored, thereby enabling effective therapeutic intervention, e.g., administration of insulin or other medicaments. For this purpose, continuous glucose monitoring (CGM) devices have been developed. Typically, a CGM device includes an in vivo glucose sensor comprising a portion, which is inserted in the user's body and which is sensitive for the level of glucose in the surrounding body fluid or tissue. A further portion of the sensor is situated outside of the user's body and provides electrical contact with an electronics unit, which is adapted for analyzing the sensor signal.

EP 3 001 952, the content of which is herein incorporated by reference, discloses a sensor system comprising a sensor adapted for transcutaneous insertion into a host's skin, a housing adapted for placement adjacent to the host skin, an electronics unit releasably attachable to the housing and an applicator configured to insert the sensor through the housing and into the host's skin. In this document, the use of conductive elastomers for connecting the sensor to the electronics unit is described.

In existing sensing devices, a preformed conductive sponge rubber is frequently used for providing electrical contact between the sensor and the electronics unit. For this purpose, small sponge rubber elements are cut from a larger bulk piece, e.g., a mat or a cord and inserted into a recess of the sensor base plate.

Producing preformed sponge rubber elements having exactly predetermined dimensions, however, is not a trivial task. If the elements are too small, they cannot provide sufficient electrical contact. On the other hand, if they are too large, the pressure on the substrate of the sensor will be too high, which also results in contacting problems.

Further, conductive sponge rubber elements are known to have abrasive properties, which can damage the conductive coating of the substrate. Additionally, the sponge rubber elements may fall out from the recess if they are not sufficiently fixed. This renders the manufacturing process even more difficult.

The biggest problem, however, is that preformed sponge rubber elements frequently cause short circuits of both substrate sides. This is due to the highly porous structure of the sponge rubber elements, whereby individual fibers may be displaced from the elements and establish an undesired contact with the second side of the sensor. This may even happen after manufacturing due to material relaxation or vibrations or shocks, e.g., when inserting the sensor into the user's body.

SUMMARY

This disclosure teaches a simple and reproducible manufacturing method of an in vivo analyte sensing device, and a novel and robust in vivo analyte sensing device, which at least partially overcome the problems of the prior art as described above.

Disclosed herein is a method of directly forming an elastomeric conductive polymer element in a recess of a raw sensor base plate, whereby a sensor base plate is obtained. For this purpose, a curable conductive polymer composition, i.e., a curable polymer composition comprising at least one electrically conductive additive, is passed, typically by injection, into a recess of a raw sensor base plate either in a free dose manner or in a closed mold under pressure and subsequently cured. Thereby, an elastomeric electrically conductive polymer element (in the following "elastomeric conductive polymer element" or "elasteromeric conductive polymer") is produced in situ, which has reproducible dimensions and firmly adheres to the sensor base plate without an externally added adhesive. Further, the elastomeric conductive polymer element has well defined physicochemical characteristics such as porosity, hardness and elasticity. Additionally, the elastomeric conductive polymer element may be produced in a much more complex three-dimensional shape than the shape of a preformed and subsequently inserted element.

A first aspect of this disclosure relates to a method of manufacturing an in vivo analyte sensing device, the method comprising the steps:

(a) providing a sensor base plate comprising at least one recess, wherein at least one elastomeric conductive polymer element is present in the at least one recess, (b) fitting a sensor with the sensor base plate wherein the sensor comprises:
   (i) a first sensor contact pad on a first side of the sensor, and
   (ii) a second sensor contact pad on a second side of the sensor, wherein the first side and the second side are different and particularly opposing each other, and wherein the first sensor contact pad is placed into electrical contact with the at least one elastomeric conductive polymer element;

(c) connecting an electronics unit with the first sensor contact pad and the second sensor contact pad, and (d) positioning a cover over the sensor base plate and the electronic unit.

In a particular embodiment of this aspect, step (a) comprises:

(a1) providing a raw sensor base plate comprising at least one recess, and (a2) passing, e.g., injecting a curable conductive polymer composition into the at least one recess of the raw sensor base plate and curing the curable conductive polymer composition wherein the at least one elastomeric conductive polymer element is formed within the at least one recess and wherein the sensor base plate is obtained.

In a further particular embodiment of this aspect, the at least one elastomeric conductive polymer element provided in step (a) is retained in the at least one recess without externally added adhesive and/or without deformation of its shape.

A further aspect of this disclosure is an in vivo analyte sensing device, which is obtainable by a manufacturing method as indicated above.

Still a further aspect of this disclosure is an in vivo analyte sensing device comprising:

(a) a sensor base plate comprising at least one recess, wherein at least one elastomeric conductive polymer element is present in the at least one recess and wherein the at least one elastomeric conductive polymer element is retained in the at least one recess without externally added adhesive and/or without deformation of its shape, (b) a sensor comprising a first portion adapted to be inserted into a user's body and a second sensor portion adapted to be outside the user's body, wherein the sensor is fitted with the sensor base plate and wherein the second sensor portion comprises
   (i) a first sensor contact pad on a first side of the second sensor portion, and
   (ii) a second sensor contact pad on a second side of the second sensor portion, wherein the first side and the second side are different, particularly opposing each other, wherein the first sensor contact pad is in electrical contact with the at least one elastomeric conductive polymer element;

(c) an electronics unit connected with the first sensor contact pad and the second sensor contact pad wherein the at least one conductive polymer element is in electrical contact with the electronics unit and (d) a cover.

Still a further aspect of this disclosure is a method of manufacturing a sensor base plate adapted for an in vivo analyte sensing device, the method comprising the steps:

(a1) providing a raw sensor base plate comprising at least one recess, and (a2) passing, e.g., injecting, a curable conductive polymer composition into the at least one recess of the raw sensor base plate and curing the curable conductive polymer composition wherein at least one elastomeric conductive polymer element is formed within the at least one recess and wherein the sensor base plate is obtained.

Still a further aspect of this disclosure is a sensor base plate, which is obtainable by a manufacturing method as indicated above.

Still a further aspect of this disclosure is a sensor base plate adapted for an in vivo analyte sensing device, comprising:

a sensor base plate comprising at least one recess, wherein at least one elastomeric conductive polymer element is present in the at least one recess and wherein the at least one elastomeric conductive polymer element is retained in the at least one recess without externally added adhesive and/or without deformation of its shape.

This disclosure relates to an in vivo analyte sensing device. In certain embodiments, the analyte sensing device is a continuous in vivo analyte monitoring device, which is adapted for measuring at least one analyte within a user's body over a predetermined time period of, e.g., about 1 day or more, or about 1 week or more, in particular about two weeks. The analyte sensing device comprises a sensor and further elements, for example, an electronics unit, which is in electrical contact with the sensor for analyzing the sensor signal, a sensor base plate, a cover, a fastening element adapted for fastening the device to the user's body and an electrical power unit, e.g., a battery. Further, the analyte sensing device may comprise a transmitter for sending signals to an external receiver.

The sensor base plate typically comprises a hole through which the sensor extends. Further, the sensor base plate may comprise a fastening element on its lower side, such as a plaster or any other adhesive element, to fix the sensor base plate on a user's skin. On the upper side of the sensor base plate the at least one recess comprising the at least one elastomeric conductive polymer element may be positioned. The electronics unit may be positioned on top of the sensor base plate and a cover may be positioned on top of the electronics unit. The cover provides a housing and serves as protection of the electronics unit against moisture, dirt and other environmental influences.

The in vivo analyte sensing device comprises a sensor, which is adapted to perform a process of detection of at least one analyte within a user's body, e.g., within the body of a human or an animal subject. In certain embodiments, the sensor is a subcutaneous or transcutaneous sensor. The sensor is adapted to determine the concentration and/or the presence of an analyte within a body fluid and/or a body tissue. As a result, at least one signal is generated, which characterizes an outcome of the detection, such as at least one measurement signal. The at least one measurement signal may comprise at least one electric signal, such as at least one voltage and/or at least one current signal. The measurement signal from the sensor is then transmitted to the electronics unit where it may be analyzed.

The sensor is adapted for measuring the concentration of a specific analyte within a user's body. The term "analyte" refers to a component or compound which may be present in the body fluid and/or tissue and the presence and/or the concentration of which is of interest for the user. For example, the analyte may be selected from the group consisting of glucose, cholesterol, triglycerides and lactate. In particular embodiments, the analyte is glucose.

The sensor typically comprises a first portion, which is an in vivo portion adapted to be inserted into the user's body, e.g., under the user's skin, and a second sensor portion, which is an ex vivo portion adapted to be fitted with a sensor base plate where an electrical contact with further elements of the sensing device, e.g., the electronics unit is provided.

The sensor may be an electrochemical sensor which is configured to conduct an electrochemical measurement in order to detect the at least one analyte contained in the body fluid and/or body tissue. The term "electrochemical measurement" refers to a detection of an electrochemical detectable property of the analyte, such as an electrochemical detection reaction. The electrochemical sensor is adapted to generate at least one electrical sensor signal, which directly or indirectly indicates the presence and/or the amount of the analyte to be determined.

The sensor comprises at least one working electrode. The sensor may comprise at least one further electrode. The at least one further electrode may be selected from the group consisting of a reference electrode, a counter electrode and a combined counter/reference electrode. In certain embodiments, the sensor comprises at least one working electrode and at least one further electrode selected from a reference electrode, a counter electrode and a combined reference/counter electrode. In particular, the sensor comprises at least one working electrode and precisely one further electrode, which is a combined counter/reference electrode. In this embodiment, the sensor is a two-electrode sensor. Thus, preferably the sensor is a two-electrode sensor.

The working electrode of the sensor is sensitive for the analyte to be detected. Typically, the working electrode comprises at least one enzyme, e.g., in immobilized form, which specifically reacts with the analyte to be detected. By means of this reaction, a signal, particularly an electrical signal is generated. The at least one working electrode may comprise precisely one enzyme or a mixture of two or more enzymes. Precisely one enzyme is preferred. Specifically, the enzyme is capable of catalyzing a chemical reaction converting the analyte. Even more specifically the at least one enzyme is selected from the group consisting of a glucose oxidase (EC 1.1.3.4), a hexose oxidase (EC 1.1.3.5), an (S)-2 hydroxy acid oxidase (EC 1.1.3.15), a cholesterol oxidase (EC 1.1.3.6), a glucose dehydrogenase (EC 1.1.1.47), a galactose oxidase (EC 1.1.3.9), an alcohol oxidase (EC 1.1.3.13), an L-glutamate oxidase (EC 1.4.3.11), and an L-aspartate oxidase (EC 1.4.3.16). In particular, the at least one enzyme is a glucose oxidase (GOx) including any modification thereof.

The at least one working electrode is typically connected to one of the first and the second contact pads via a conductive trace.

The at least one further electrode is typically connected via a further conductive trace to the first or second contact pad to which the at least one working electrode is not connected. Thus, if the at least one working electrode is connected to the first contact pad, then the at least one further electrode is connected to the second contact pad and vice versa. The at least one working electrode and the at least one further electrode are typically located on the side of the sensor, on which the contact pad to which they are connected is located.

The terms “conductive trace” and “further conductive trace” within the context of this disclosure refer, without limitations, to an electrically conductive strip, layer, wire or other type of a conductive material. Suitable conductive materials are known as such and are, for example, selected from the group consisting of gold, nickel, platinum, palladium, carbon and carbon paste. Parts of the conductive traces may be covered at least partially by an insulating material, such as a solder resist. This is known as such.

The second sensor portion, i.e., the ex vivo portion, is located outside the user’s body for transmitting the measurement signal to an electronics unit wherein the signal may be analyzed. The sensor is fitted with the sensor base plate for providing physical support, e.g., by positioning the sensor in or on the sensor base plate and for providing appropriate electrical connection with the electronics unit. The electrical connection between the sensor and the electronics unit may be an indirect connection, e.g., via the elastomeric conductive polymer element, or a direct connection, e.g., via a physical contact between the sensor and the electronics unit. “Electrical connection between the sensor and the electronics unit” within the context of this disclosure in particular means that there is an electrical connection between the first sensor contact pad and the electronics unit as well as between the second sensor contact pad and the electronics unit. Details of this connection are described in further detail below.

The second sensor portion, i.e., the ex vivo portion comprises a first sensor contact pad on a first side thereof and a second sensor contact pad on a second side thereof, wherein the first side and the second side are typically different from each other. In certain embodiments, the first side and the second side are opposing each other. The first and the second sensor contact pads are not in direct electrical contact with each other. It is clear, that the first sensor contact pad and the second contact pad are in contact via the electronics unit. The first sensor contact pad is adapted to be in electrical contact with the at least one elastomeric conductive polymer element in the at least one recess of the sensor base plate. The elastomeric conductive polymer is further in electrical contact with a first contact site on the electronics unit in order to provide an electrical connection between the first sensor contact pad and the electronics unit. By this means, an electrical contact between the first sensor contact pad and the first contact site on the electronics unit is provided. The second sensor contact pad is typically not in electrical contact with the at least one elastomeric conductive polymer element. The second sensor contact pad may be in direct contact with a second contact site on the electronics unit, which is electrically separated from the first contact site on the electronics unit.

The first sensor contact pad and the second sensor contact pad usually comprise a conductive material. Typically, the first sensor contact pad and the second sensor contact pad comprise the same conductive material as the respective conductive trace.

The sensor base plate is manufactured from a raw sensor base plate, which typically comprises and particularly consists of a non-conductive material, e.g., a non-conductive polymer. In certain embodiments, the raw sensor base plate comprises and particularly consists of a thermoplastic polymer, particularly of a substantially rigid thermoplastic polymer such as polymethyl methacrylate (PMMA), polycarbonate (PC), ABS (acrylonitrile-butadiene-styrene) PPA (aliphatic polyamide), POM (polyoxymethylene), PP (polypropylene), PBT (poly(butylene terephthalate)), PPSU (poly (phenylsulfone)), PEEK (poly(etheretherketone)), PEI (polyetherimide).

The raw sensor base plate may be produced by any suitable method for obtaining a suitable three-dimensional shape such as molding, e.g., injection molding. In certain embodiments, the raw sensor plate is manufactured by passing, e.g., injecting, a curable sensor plate polymer composition into a mold and forming the sensor base plate by curing the curable sensor plate polymer composition in the mold. In this context, the term “curing” involves thermal curing, e.g., by physical solidification and/or induced curing, e.g., by radiation and/or chemically induced processes as known in the art.

The raw sensor base plate comprises at least one recess wherein the elastomeric conductive polymer element is formed in situ. The sensor base plate, i.e., the raw sensor base plate including the elastomeric conductive polymer element, is provided with a shape, which provides physical support for the sensor and allows establishing an electrical contact of the sensor with an electronics unit, which may comprise a printed circuit board (PCB) having electrical contact sites for connecting with the sensor, particularly wherein the first sensor contact pad is connected via the elastomeric conductive polymer element with the first contact site on the electronics unit and wherein the second sensor contact pad is directly connected with the second contact site on the electronics unit.

In certain embodiments, the sensor base plate has an essentially circular shape except for one region, which may have an essentially straight edge to avoid rotation of the base plate in its housing. The diameter of the base plate is typically between about 2.5 cm and about 4 cm. The at least one recess may have a length of about 2 mm to about 6 mm, e.g., about 4 mm, a width of about 0.5 mm to about 2 mm, e.g., about 1 mm and a depth from about 0.5 mm to about 2 mm, e.g., about 1 mm.

According to this disclosure, an electrical contact between the first sensor contact pad and the electronics unit is provided via at least one elastomeric conductive polymer element, which has been formed by passing, e.g., injecting, a curable conductive polymer composition into at least one recess of the raw sensor base plate and subsequent curing in the at least one recess. Thereby, an elastomeric conductive polymer element is produced in situ in a recess of the raw sensor base plate and the sensor base plate is obtained. Typically, the curable conductive polymer composition is in a fluid form, e.g., in a molten form, which allows passing into the at least one recess of the raw sensor base plate. The term "passing" includes any means of transporting the curable conductive polymer composition into the at least one recess of the raw sensor base plate. In certain embodiments, the term "passing" comprises injecting. The curable conductive polymer composition may be passed, e.g., injected, into the at least one recess in a free-dose manner or in the presence of a mold. In certain embodiments, the curable conductive polymer composition is injection-molded into the at least one recess and subsequently cured.

The at least one elastomeric conductive polymer element can be manufactured from any suitable type of curable conductive polymer composition. For example, the elastomeric conductive polymer element may comprise a polyolefin-based polymer such as polyethylene or polypropylene, a polystyrene-based polymer, a polyurethane or polyurea-based polymer, a poly(meth)acrylic-based polymer such as acrylonitrile, a polyacrylate or a polymethacrylate, or an acrylonitrile-butadiene-styrene copolymer or any mixture thereof.

The elastomeric conductive polymer element further comprises an electrically conductive additive, e.g., conductive fibers and/or particles, particularly selected from carbon fibers and/or particles, metal fibers and/or particles and metal-coated carbon fibers and/or particles. In specific embodiments, the electrically conductive additive is selected from polyacrylonitrile- and/or pitch-based carbon fibers or particles, metal-coated carbon fibers and stainless steel fibers.

Typically, the curable conductive polymer composition is passed, e.g., injected into the recess in fluid form, e.g., molten form. Thereafter, the polymer composition is cured in situ, i.e., within the at least one recess, whereby the elastomeric conductive polymer element is obtained. The term "curing" involves thermal curing, e.g., by physical solidification and/or induced curing, e.g., by radiation and/or chemically induced processes as known in the art.

In certain embodiments, the elastomeric conductive polymer element may have a size (volume) from about 0.004 $mm^3$ (e.g., length about 0.4 mm, width about 0.1 mm and height about 0.1 mm) to about 500 $mm^3$ (e.g., length 20 mm, width about 5 mm, height about 5 mm). In particular embodiments, the size (volume) of the elastomeric conductive polymer element is from about 1 $mm^3$ to about 10 $mm^3$ such as about 5.5 $mm^3$ (e.g., length about 3.9 mm, width about 1.1 mm and height about 1.3 mm). Further, the elastomeric conductive polymer element may have at least one of the following physico-chemical parameters:

- conductivity from about 0.000001 S/cm to about 0.1 S/cm,
- porosity from about 0% to about 80%,
- density from about 0.1 $g/cm^3$ to about 1.5 $g/cm^3$,
- hardness from about Shore 100 A to about 25 A, and
- tensile elongation at yield from about 50 to about 1000% (break, die C: 0.125 in, 20 in/min (3.2 mm, 500 mm/min)).

According to this disclosure, the elastomeric conductive polymer element is retained in the recess without externally added adhesive and/or without deformation of its shape, i.e., it cannot fall out under action of gravity. In contrast to a preformed sponge rubber element, which is inserted as a piece of solid material into the recess, the elastomeric conductive polymer element is formed in situ within the recess. Thereby, it may adhere to the surface of the sensor base plate in the at least one recess without added external adhesive and/or held in the at least one recess by physical retention without deformation.

In certain embodiments, the elastomeric conductive polymer element is retained in the recess by adhering to the surface of the recess without an externally added adhesive. This may be effected by passing, e.g., injecting, the curable conductive polymer composition into the at least one recess of the raw sensor base plate at an elevated temperature, which is sufficiently high to softening and/or slightly melting the surface of the raw sensor base plate within the recess, whereby the elastomeric conductive polymer element after curing adheres to the surface of the sensor base plate within the recess.

In further embodiments, the elastomeric conductive polymer element is held in the recess by physical retention, e.g., by physical retention alone without deformation of its shape. According to these embodiments, the retention may be provided by the in situ formation of the elastomeric conductive polymer element within the recess by passing, e.g., injecting the curable conductive polymer composition into the recess and subsequent curing of the curable conductive polymer composition within the recess, whereby the resulting elastomeric conductive element is formed in close contact with the bottom and the walls the recess, particularly without substantial voids between the elastomeric conductive polymer element and the bottom and the walls of the recess. In certain embodiments, the recess may have a shape, which is adapted to promote retention of the elastomeric conductive polymer element. For example, the recess may have a tapered shape in a direction towards its upper rim, i.e., a shape, wherein the cross-section of the recess at or close to its bottom is larger than the cross-section of the recess at or close to its upper rim. The term "bottom" means the part of the recess, which is distal from the surface of the sensor base plate. The term "upper rim" means the part of the recess, which is proximal to the surface of the sensor base plate. According to these embodiments, softening or melting the surface of the sensor base plate within the recess during the formation of the elastomeric conductive polymer element may not be required.

In particular embodiments of this disclosure, the manufacturing process of the sensor base plate is an integrated process, wherein in a first step the raw sensor base plate is formed and in a second step the elastomeric conductive polymer element is formed in situ in a recess of the raw sensor base plate, wherein the manufacturing process is carried out in a single manufacturing device, e.g., in a single injection molding device.

In certain embodiments, the sensor base plate including the elastomeric conductive polymer element is manufactured by two-component molding, e.g., two-component injection molding. In a first step, the raw sensor plate is manufactured by passing a curable sensor plate polymer composition into a suitable mold, e.g., by injection molding, and curing the curable sensor plate polymer composition, wherein a raw sensor base plate is obtained and wherein in a second step the at least one elastomeric conductive polymer element is formed in the at least one recess of the raw sensor base plate while the raw sensor base plate is still in the mold. Such two-component molding, e.g., injection molding techniques are well known in the art and e.g., described in WO 03/044816, the content of which is herein incorporated by reference.

In particular embodiments, the manufacturing process comprises passing, e.g., injecting, the curable conductive polymer composition into the recess through a passage in the raw sensor base plate, particularly from a side of the sensor plate which is distal from the side where the recess is located. Thus, if the recess is located on the upper side of the raw sensor base plate, the curable conductive polymer composition is passed, e.g., injected through the raw sensor base plate from its lower side. In this embodiment, a mold may be placed over the opening of the recess, whereby a cavity for the curable conductive polymer composition is formed. After passing, e.g., injecting the curable conductive polymer composition into the cavity and curing, the surface of the mold defines an outward surface of the elastomeric conductive polymer element, wherein the outward surface is distal from the sensor base plate and faces away from the bottom of the recess. Thereby, an elastomeric conductive polymer element having a clean and well-defined outward surface is obtained. In certain embodiments, the outward surface of the elastomeric conductive polymer element comprises a three-dimensional shape, e.g., a structure such as a recess adapted for receiving and/or supporting the sensor.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
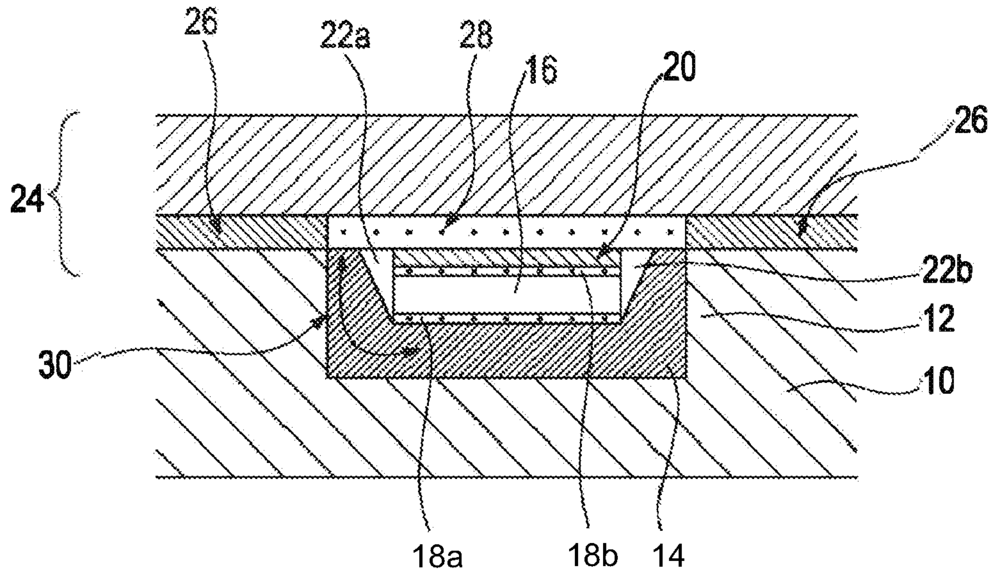
FIG. 1 schematically depicts a sensing device having a sensor contacting an electronics unit via an electrically conductive rubber sponge.

FIG. 1 schematically depicts a prior art sensing device comprising a sensor contacting an electronics unit via a flexible electrically conductive rubber sponge element. The sensing device comprises a sensor base plate (10) having a recess (12). Within the recess (12), a cut piece of conductive rubber sponge (14) is inserted. A sensor (16) is inserted on top of the conductive rubber sponge (14), which thereby is deformed. The upper and lower sides of the sensor may be coated with a conductive material such as a metal, e.g., gold layer (18*a*, 18*b*). The gold layer on the lower side (18*a*) forms a first sensor contact pad, which is in electrical contact with the deformed rubber sponge (14). On the other side, i.e., the upper side, the gold layer (18*b*) is overlaid with a non-conductive layer, e.g., photo resist (20). A part of the gold layer (18*b*) of the upper side is left open forming the second sensor contact pad which may contact the second contact site of the electronics unit (not shown). Further, due to the deformation of the rubber sponge (14), voids (22*a*, 22*b*) are present. The sensor (16) is aligned with an electronics unit (24) comprising a printed circuit board (PCB) or a printed circuit board assembly (PCBA). A part of the electronics unit (24) is coated with a non-conductive layer, e.g., photo resist (26) and a further part of the electronics unit (24) is coated with a conductive layer (28), e.g., a metal such as gold. An electrical contact between sensor contact pad (18*a*) and the first contact site (28) on the electronics unit (24) is provided via the deformed rubber sponge (14) as shown by an arrow (30).

The use of a cut piece of a rubber sponge (14) is however associated with substantial difficulties as indicated supra. Replacement of sponge rubber element (14) by an elastomeric conductive polymer, which has been formed in situ within the recess (12) and is thereby retained within the recess, e.g., by adhering to its surface without externally added adhesive and/or by physical retention without deformation of its shape, can overcome these problems.

Figure 2:
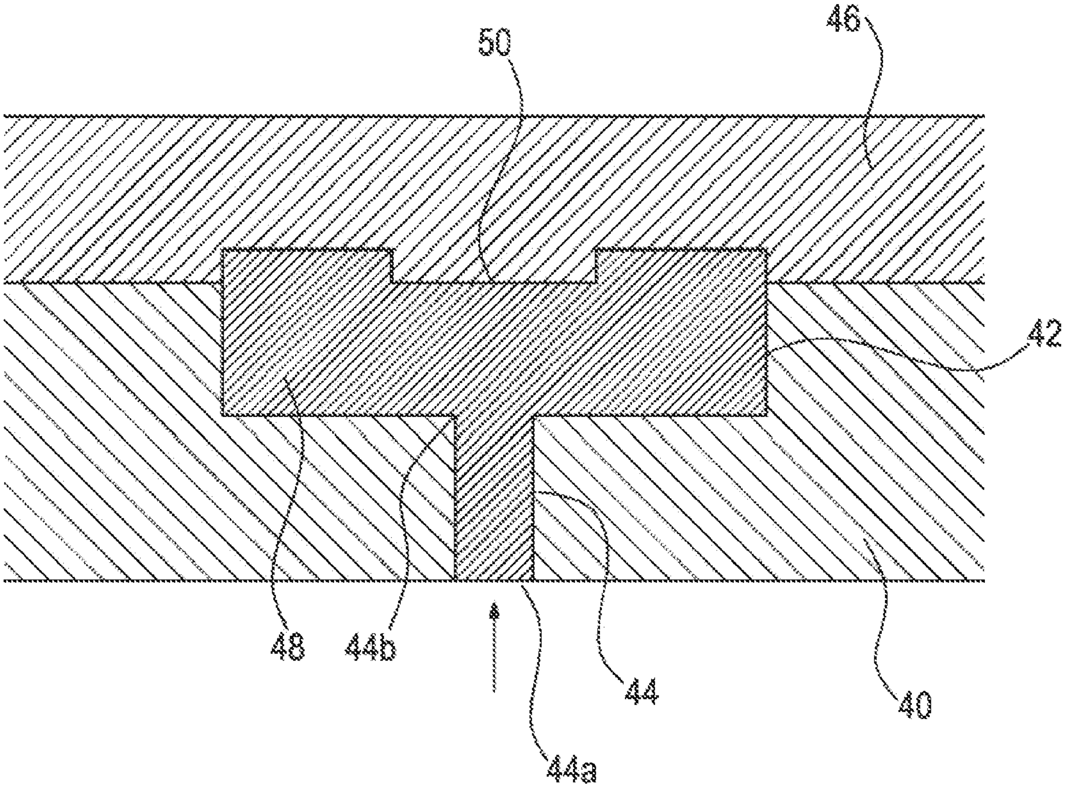
FIG. 2 schematically depicts another embodiment of a sending device having a sensor contacting an electronics unit via a flexibly electrically conductive element.

FIG. 2 schematically depicts an embodiment of this disclosure, wherein an elastomeric polymer conductive element is formed in a recess of a raw sensor base plate by injection molding through the sensor base plate. A raw sensor base plate (40) is provided comprising at least one recess (42). A passage (44) extends between openings (44*a*, 44*b*) through the sensor base plate (40) to the recess (42). The passage can be provided during and/or after the manufacturing of the raw sensor base plate, e.g., by using an appropriate mold and/or by drilling. A mold (46), e.g., an injection mold is provided for covering the outer surface of recess (42) thereby forming a cavity defined by the surfaces of the mold (46) and the recess (42). A curable elastomeric polymer composition (48) is passed through the passage (44) from opening (44*a*) to opening (44*b*) and then into the cavity defined by the recess (42) and the mold (46). Subsequently, the composition (48) is cured in situ within the cavity. Thereby, an elastomeric conductive polymer element is obtained. The outward surface of the elastomeric conductive polymer element, i.e., the surface distal from the recess (42) is defined by the surface of the mold (46). Thus, an elastomeric conductive polymer element having a well-defined surface with a three-dimensional shape, e.g., a structure (50) including a recess for receiving a sensor (not shown) is provided.

Further, this disclosure is described without any limitation by the following embodiments of the specification.

Embodiment 1: A method of manufacturing an in vivo analyte sensing device, the method comprising the steps:

(a) providing a sensor base plate comprising at least one recess, wherein at least one elastomeric conductive polymer element is present in the at least one recess, (b) fitting a sensor with the sensor base plate wherein the sensor comprises:

(i) a first sensor contact pad on a first side of the sensor, and (ii) a second sensor contact pad on a second side of the sensor, wherein the first side and the second side are different and particularly opposing each other, and wherein the first sensor contact pad is placed into electrical contact with the at least one elastomeric conductive polymer element;

(c) connecting an electronics unit with the first sensor contact pad and the second sensor contact pad, and (d) positioning a cover over the sensor base plate and the electronic unit.

Embodiment 2: The method of Embodiment 1, wherein in step (a) the at least one elastomeric conductive polymer element is retained in the at least one recess without externally added adhesive and/or without deformation of its shape.

Embodiment 3: The method of Embodiments 1 or 2, wherein the analyte is selected from glucose, cholesterol, triglycerides, and lactate.

Embodiment 4: The method of any one of Embodiments 1-3, wherein the analyte is glucose.

Embodiment 5: The method of any one of Embodiments 1-4, wherein step (a) comprises:

(a1) providing a raw sensor base plate comprising at least one recess, and (a2) passing, e.g., injecting a curable conductive polymer composition into the at least one recess of the raw sensor base plate and curing the curable conductive polymer composition wherein the at least one elastomeric conductive polymer element is formed within the at least one recess and wherein the sensor base plate is obtained.

Embodiment 6: The method of Embodiment 5, wherein steps (a1) and (a2) are performed as an integrated process, which is carried out in a single manufacturing device.

Embodiment 7: The method of Embodiment 6, wherein the sensor base plate is manufactured by two-component molding, e.g., two-component injection molding, wherein in a first step, the raw sensor plate is manufactured by passing, e.g., injecting, a curable sensor plate polymer composition into a mold and forming the raw sensor base plate by curing the curable sensor plate polymer composition in the mold, and wherein in a second step, the at least one elastomeric conductive polymer element is formed in the at least one recess of the raw sensor base plate while the raw sensor base plate is still in the mold.

Embodiment 8: The method of any one of Embodiments 5-7, wherein the manufacturing process comprises passing, e.g., injecting the curable conductive polymer composition into the at least one recess through a passage extending through the raw sensor base plate.

Embodiment 9: The method of Embodiment 8, wherein a mold is placed over the open side of the recess, wherein the surfaces of the mold and the recess define a cavity for the curable conductive polymer composition, wherein after passing the curable conductive polymer composition into the cavity and curing, the surface of the mold defines an outward surface of the elastomeric conductive polymer element, wherein the outward surface is distal from the sensor base plate.

Embodiment 10: The method of any one of Embodiments 1-9, wherein the raw sensor base plate comprises and preferably consists of a non-conductive material, particularly of a non-conductive polymer.

Embodiment 11: The method of any one of Embodiments 1-10, wherein the raw sensor base plate comprises and preferably consists of a thermoplastic polymer, particularly of a substantially rigid thermoplastic polymer.

Embodiment 12: The method of any one of Embodiments 1-11, wherein the at least one elastomeric conductive polymer element comprises an elastomeric polymer selected from a polyolefin-based polymer such as polyethylene or polypropylene, a polystyrene-based polymer, a polyurethane or polyurea-based polymer, a poly(meth)acrylic-based polymer such as acrylonitrile, a polyacrylate or a polymethacrylate, or an acrylonitrile-butadiene-styrene copolymer or any mixture thereof.

Embodiment 13: The method of any one of Embodiments 1-12, wherein the at least one elastomeric conductive polymer element comprises a conductive additive, e.g., conductive fibers and/or particles, particularly selected from carbon fibers and/or particles, metal fibers and/or particles and metal-coated carbon fibers and/or particles.

Embodiment 14: The method of any one of Embodiments 1-13, wherein the sensor is a two-electrode sensor.

Embodiment 15: The method of any one of Embodiments 1-14, wherein the sensor comprises at least one working electrode, which is specific for the analyte to be detected.

Embodiment 16: The method of any one of Embodiments 1-15, wherein the sensor comprises at least one working electrode and at least one further electrode, wherein the at least one further electrode is selected from the group consisting of at least one counter electrode, at least one reference electrode and at least one combined counter/reference electrode.

Embodiment 17: The method of any one of Embodiments 1-16, wherein the first and the second sensor contact pads are connected to different electrodes of the sensor, particularly wherein the first sensor contact pad is connected to a working electrode and the second sensor contact pad is connected to at least one further electrode or vice versa.

Embodiment 18: The method of any one of Embodiments 1-17, wherein the second sensor contact pad is not in contact with the elastomeric conductive polymer.

Embodiment 19: The method of any one of Embodiments 1-18, wherein the second sensor contact pad is in direct electrical contact with the electronics unit, wherein the electrical contact between the first sensor contact pad and the electronics unit is electrically separated from the electrical contact between the second sensor pad and the electronics unit.

Embodiment 20: An in vivo analyte sensing device obtainable by a method of any one of Embodiments 1-19.

Embodiment 21: An in vivo analyte sensing device, particularly obtainable by a method of any one of Embodiments 1-20 comprising:

a) a sensor base plate comprising at least one recess, wherein at least one elastomeric conductive polymer element is present in the at least one recess and wherein the at least one elastomeric conductive polymer element is retained in the at least one recess without externally added adhesive and/or without deformation of its shape, (b) a sensor comprising a first portion adapted to be inserted into a user's body and a second sensor portion adapted to be outside the user's body, which is fitted with the sensor base plate, wherein the second sensor portion comprises:

(i) a first sensor contact pad on a first side of the second sensor portion, and (ii) a second sensor contact pad on a second side of the second sensor portion, wherein the first side and the second side are different, particularly opposing each other, wherein the first sensor contact pad is in electrical contact with the at least one elastomeric conductive polymer element;

(c) an electronics unit connected with the first sensor contact pad and the second sensor contact pad wherein the at least one conductive polymer element is in electrical contact with the electronics unit and (d) a cover.

Embodiment 22: The sensing device of Embodiments 20 or 21 further comprising at least one of (e) an electrical power unit, and (f) a fastening element adapted for fasting the device to the user's body.

Embodiment 23: The sensing device of any one of Embodiments 20-22, wherein the at least one elastomeric conductive polymer element is retained in the at least one recess by adhering to the surface of the at least one recess without externally added adhesive.

Embodiment 24: The sensing device of any one of Embodiments 20-22, wherein the at least one elastomeric conductive polymer element is retained in the at least one recess by physical retention without deformation of its shape.

Embodiment 25: A method of measuring an analyte in vivo, comprising using a sensing device of any one of Embodiments 20-24.

Embodiment 26: A method of manufacturing a sensor base plate adapted for an in vivo analyte sensing device, the method comprising the steps:

(a1) providing a raw sensor base plate comprising at least one recess, and (a2) passing, e.g., injecting, a curable conductive polymer composition into the at least one recess of the raw sensor base plate and curing the curable conductive polymer composition wherein at least one elastomeric conductive polymer element is formed within the at least one recess and wherein the sensor base plate is obtained.

Embodiment 27: The method of Embodiment 26, wherein the curable conductive polymer composition is passed, e.g., injected, into the at least one recess in a free-dose manner or in the presence of a mold.

Embodiment 28: The method of Embodiments 26 or 27, wherein step (a1) comprises forming the raw sensor base plate body by injection-molding.

Embodiment 29: The method of any one of Embodiments 26-28, wherein steps (a1) and (a2) are performed as an integrated process, which is carried out in a single manufacturing device.

Embodiment 30: The method of Embodiment 29, wherein the sensor base plate is manufactured by two-component molding, e.g., two-component injection molding, wherein in a first step, the raw sensor plate is manufactured by passing, e.g., injecting, a curable sensor plate polymer composition into a mold and forming the raw sensor base plate by curing the curable sensor plate polymer composition in the mold, and wherein in a second step, the at least one elastomeric conductive polymer element is formed in the at least one recess of the raw sensor base plate while the raw sensor base plate is still in the mold.

Embodiment 31: The method of any one of Embodiments 26-30, wherein step (a2) comprises passing, e.g., injecting the curable conductive polymer composition into the at least one recess through a passage extending through the raw sensor base plate.

Embodiment 32: The method of Embodiment 31, wherein a mold is placed over the open side of the recess, and wherein the surfaces of the mold and the recess define a cavity for the curable conductive polymer composition, wherein after passing the curable conductive polymer composition into the cavity and curing, the surface of the mold defines an outward surface of the elastomeric conductive polymer element, wherein the outward surface is distal from the sensor base plate.

Embodiment 33: A sensor base plate obtainable by the method of any one of Embodiments 26-32.

Embodiment 34: A sensor base plate adapted for an in vivo analyte sensing device, particularly obtainable by the method of any one of Embodiments 26-32, comprising a raw sensor base plate comprising at least one recess, wherein at least one elastomeric conductive polymer element is present in the at least one recess and wherein the at least one elastomeric conductive polymer element is retained in the at least one recess without externally added adhesive and/or without deformation of its shape.

Embodiment 35: The sensor base plate of Embodiment 34, wherein the at least one elastomeric conductive polymer element is retained in the at least one recess by adhering to the surface of the at least one recess without externally added adhesive.

Embodiment 36: The sensor base plate of Embodiment 34, wherein the at least one elastomeric conductive polymer element is retained in the at least one recess by physical retention without deformation of its shape.

Embodiment 37: Use of the sensor base plate of any one of Embodiments 33-36 for the manufacture of an in vivo analyte sensor.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method of manufacturing an in vivo analyte sensor assembly, comprising:

(a) providing a sensor base plate having a recess with an elastomeric conductive polymer disposed in the recess, the elastomeric conductive polymer being retained in the recess without externally added adhesive and/or without deformation;

(b) fitting a sensor with the sensor base plate, wherein the sensor comprises a first sensor contact pad on a first side of the sensor and a second sensor contact pad on a second side of the sensor, wherein the first and second sides oppose each other and the first sensor contact pad is placed into electrical contact with the elastomeric conductive polymer;

(c) connecting an electronics unit with the first sensor contact pad and the second sensor contact pad; and (d) positioning a cover over the sensor base plate and the electronics unit.

2. The method of claim 1, wherein the in vivo analyte sensor assembly is configured to measure glucose.

3. The method of claim 1, wherein step (a) comprises:

(a1) providing a raw sensor base plate with the recess; and (a2) passing a curable conductive polymer composition into the recess and curing the curable conductive polymer composition, wherein the elastomeric conductive polymer is formed within the recess and wherein the sensor base plate is obtained.

4. The method of claim 3, wherein steps (a1) and (a2) are performed as an integrated process carried out in a single manufacturing device.

5. The method of claim 4, wherein the sensor base plate is manufactured by two-component molding, wherein in a first step the raw sensor base plate is manufactured by passing a curable sensor plate polymer composition into a mold and forming the raw sensor base plate by curing the curable sensor plate polymer composition in the mold, and wherein in a second step the elastomeric conductive polymer is formed in the recess while the raw sensor base plate is still in the mold.

6. The method of claim 3, wherein the manufacturing process comprises passing the curable conductive polymer composition into the recess through a passage extending through the raw sensor base plate, wherein a mold is placed over an open side of the recess and wherein the surfaces of the mold and the recess define a cavity for the curable conductive polymer composition, wherein after passing the curable conductive polymer composition into the cavity and curing, the surface of the mold defines an outward surface of the elastomeric conductive polymer, wherein the outward surface is distal from the sensor base plate.

7. The method of claim 1, wherein the sensor is a two-electrode sensor and wherein the first and the second sensor contact pads are connected to different electrodes of the sensor.

8. The method of claim 1, wherein the sensor comprises at least one working electrode, which is specific for an analyte to be detected, and wherein the sensor comprises a further electrode selected from the group consisting of a counter electrode, a reference electrode and a combined counter/reference electrode.

9. The method of claim 1, wherein the second sensor contact pad is not in contact with the elastomeric conductive polymer.

* * * * *